United States Patent
Huang et al.

(10) Patent No.: US 7,276,088 B2
(45) Date of Patent: Oct. 2, 2007

(54) HAIR COLORING AND COSMETIC COMPOSITIONS COMPRISING CARBON NANOTUBES

(75) Inventors: Xueying Huang, Hockessin, DE (US); Robert K. Kobos, Wilmington, DE (US); Gann Xu, Boothwyn, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/093,533

(22) Filed: Mar. 30, 2005

(65) Prior Publication Data
US 2005/0229334 A1   Oct. 20, 2005

Related U.S. Application Data

(60) Provisional application No. 60/562,507, filed on Apr. 15, 2004.

(51) Int. Cl.
*A61K 7/13* (2006.01)

(52) U.S. Cl. .................. 8/405; 8/406; 8/407; 8/448; 8/493; 8/551; 8/552; 8/554; 8/637.1; 132/202; 132/208

(58) Field of Classification Search .......... 8/405, 8/406, 448, 493, 552, 554, 587, 594, 637.1, 8/551, 407; 132/202, 208
See application file for complete search history.

(56) References Cited

U.S. PATENT DOCUMENTS

| | | | |
|---|---|---|---|
| 4,559,057 | A | 12/1985 | Bogaty et al. |
| 5,597,386 | A | 1/1997 | Igarashi et al. |
| 2002/0034480 | A1 | 3/2002 | Grimm et al. |
| 2002/0041854 | A1 | 4/2002 | Hadasch et al. |
| 2003/0039604 | A1 | 2/2003 | Niu et al. |
| 2003/0086858 | A1 | 5/2003 | Niu et al. |
| 2003/0185870 | A1 | 10/2003 | Grinstaff et al. |
| 2004/0010864 | A1 | 1/2004 | Vic et al. |
| 2004/0115232 | A1* | 6/2004 | Giroud et al. .............. 424/401 |

OTHER PUBLICATIONS

Yongfu Lian et al., Assignment of the Fine Structure in the Optical Absorption Spectra of Soluble Single-Walled Carbon Nanotubes, J. Phys. Chem. B, 107:12082-12087, 2003.

Francisco Carrasco-Marin et al., Water adsorption on activated carbons with different degrees of oxidation, J. Chem. Soc., Faraday Trans., 93(12):2211-2215, 1997.

Eric Langenmayr et al., Carbon Black dispersions for High Optical Density on Plain Paper, IS&T's NIP19: 2003 International Conference on Digital Printing Technologies pp. 199-202.

* cited by examiner

*Primary Examiner*—Eisa Elhilo

(57) ABSTRACT

The invention provides new hair colorant and cosmetic compositions comprising carbon nanotubes that have either been chemically functionalized or physically modified to increase their affinity for hair.

2 Claims, 3 Drawing Sheets

(1) Carbon Nanotube Surface Functionization (2) Hair Coloring with Polyamines to Enhance the Binding

US 7,276,088 B2

HAIR COLORING AND COSMETIC COMPOSITIONS COMPRISING CARBON NANOTUBES

This application claims the benefit of U.S. Provisional Application 60/562,507, filed on Apr. 15, 2004, now pending.

FIELD OF INVENTION

The invention relates to the field of personal care products. More specifically, the invention relates to hair coloring and cosmetic compositions comprising chemically functionalized or physically modified carbon nanotubes as a black pigment.

BACKGROUND OF THE INVENTION

Hair coloring compositions contain various types of coloring agents, specifically, permanent, semi-permanent or direct, and temporary colorants. The permanent hair dyes are generally oxidative dyes that provide hair color that lasts about four to six weeks. These oxidative hair dyes consist of two parts; one part contains the oxidative dyes in addition to other ingredients, while the second part contains an oxidizing agent such as hydrogen peroxide. The two components are mixed immediately prior to use. The oxidizing agent oxidizes the dye precursors, which then combine to form large color molecules within the hair shaft. Although the oxidative hair dyes provide long-lasting color, the oxidizing agents they contain cause hair damage. The semi-permanent or direct hair dyes are preformed dye molecules that are applied to the hair and provide color for about six to twelve shampoos. This type of hair dye is gentler to the hair because it does not contain peroxides, but the hair color does not last as long. Temporary hair dyes are dye molecules or pigments that are too large to diffuse into the hair shaft, and therefore act on the exterior of the hair. Consequently, temporary hair dyes are generally removed after one or two shampoos.

Carbon black has been used as a temporary hair dye in hair coloring compositions, particularly for covering white or gray hair (Bogaty et al. U.S. Pat. No. 4,559,057). Additionally, carbon black has been used as a pigment in cosmetic formulations such as eye shadow, eyeliner, and mascara (Hadasch et al. U.S. Patent Application Publication No. 2002/0041854, and Grimm et al. U.S. Patent Application Publication No. 2002/0034480). Carbon black provides good covering properties, but has a weak interaction with the hair so that the adherence of the pigment to the hair is poor. Consequently, the carbon black color is readily transferred to clothing, skin, combs, brushes, and other contacting surfaces. To enhance the interaction of the carbon black pigment with hair, Igarashi et al. (U.S. Pat. No. 5,597,386) used anti-hair antibody attached to carbon black as a hair colorant. Although this method results in stronger attachment of the carbon black to hair, the antibodies are expensive and difficult to produce.

Carbon nanotubes (CNT) have been the subject of intense research since their discovery in 1991. Carbon nanotubes possess unique properties such as small size, considerable stiffness, and electrical conductivity, which make them suitable in a wide range of applications. Carbon nanotubes may be either multi-walled (MWNTs) or single-walled (SWNTs), and have diameters in the nanometer range. However, the use of carbon nanotubes as a pigment in hair coloring and cosmetic compositions has not been described.

Therefore, the need exists for a black pigment for use in hair coloring and cosmetic compositions that has enhanced interaction with hair fibers to give a more durable coloring effect.

Applicants have solved the stated problem by discovering that chemically functionalized and physically modified carbon nanotubes function as an effective black pigment in hair coloring and cosmetic compositions. The carbon nanotubes provide significant advantages for high performance hair coloring without damaging the hair. The small size of the nanotubes, typically, a few nanometers in diameter, provides a thin coating that results in a smooth feeling to the hair, while producing a volumizing effect. Additionally, the increased surface area of carbon nanotubes compared to carbon black results in enhanced contact and interaction with the hair for a longer-lasting coloring effect.

SUMMARY OF THE INVENTION

The invention relates to the use of functionalized carbon nanotubes for use in hair care and cosmetic applications. The carbon nanotubes of the invention may be chemically functionalized, producing surface functional groups that have affinity for hair. Additionally the carbon nanotubes may be physically modified with a modifying agent such as a polymer, which has affinity for hair.

Accordingly it is an object of the invention to provide a hair colorant or cosmetic composition comprising: a chemically functionalized carbon nanotube, or a physically modified carbon nanotube.

Hair or cosmetic compositions of the invention may be made according to a process comprising the steps of
  a) providing a population of undispersed carbon nanotubes in solution;
  b) contacting the carbon nanotubes of (a) with a radical generating agent in the presence of acid for a time sufficient to permit the carbon nanotubes to disperse; and
  c) optionally recovering the carbon nanotubes.

Additionally it is an object of the invention to provide a method of dyeing hair, eyebrows or eyelashes comprising:
  a) providing a hair colorant comprising either a chemically functionalized or physically modified carbon nanotube; and
  b) contacting the hair colorant of (a) with hair, eyebrows, or eyelashes for a time sufficient for the carbon nanotubes to bind to hair wherein the hair, eyebrows or eyelashes are dyed.

DETAILED DESCRIPTION OF THE INVENTION

Figure 1:
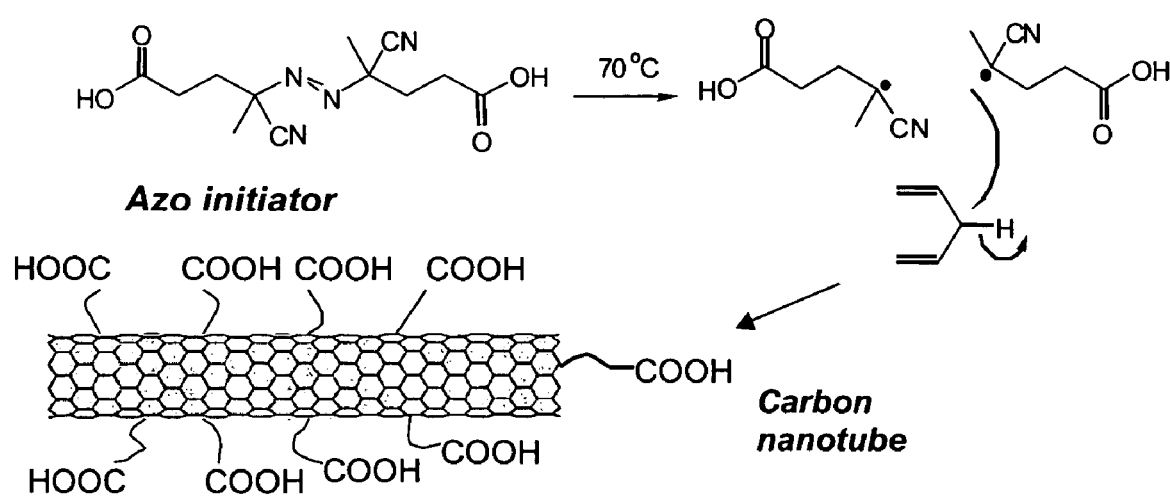
FIG. 1. A schematic illustration of chemically functionalizing carbon nanotubes with an azo initiator.

The invention provides hair coloring and cosmetic compositions comprising chemically functionalized or physically modified carbon nanotubes. The carbon nanotubes provide significant advantages for high performance hair coloring without damaging the hair. The small size of the nanotubes, typically, a few nanometers in diameter, provides a thin coating that results in a smooth feeling to the hair, while producing a volumizing effect. Additionally, the increased surface area of the carbon nanotubes compared to carbon black results in enhanced contact and interaction with the hair for a longer-lasting coloring effect. The invention is useful because the hair coloring and cosmetic compositions comprising carbon nanotubes have use in various personal care products, including, but not limited to, hair colorants, eye shadow, eyeliner, eyebrow pencil, and mascara.

The following definitions are used herein and should be referred to for interpretation of the claims and the specification.

"CNT" means carbon nanotube.

"MWNT" means multi-walled nanotube.

"SWNT" means single walled nanotube.

The term "chemically functionalized carbon nanotubes" refers to carbon nanotubes that have been chemically treated to introduce functional groups on the surface. Chemical treatments include, but are not limited to, oxidation, radical initiation reactions, and Diels-Alder reactions.

The term "physically modified carbon nanotubes" refers to carbon nanotubes that have been dispersed by physical means, for example, ultrasonication, or have been coated with or are associated with a modifying agent.

The term "modifying agent" refers to reagents used to coat carbon nanotubes to disperse them in aqueous solution. Modifying agents include, but are not limited to, surfactants, such as sodium dodecylsulfate, alkyl benzene sulfonate, dextrin, polyethylene oxide, alkyl-ether sulfonate and Triton® series compounds; organic polymers, such as polyamines, anionic polymers, cationic polymers, polyvinylpyrrolidone, polysaccharides, gum arabic, polystyrene sulfonate; biopolymers, such as peptides, proteins and nucleic acids; and nanoparticles. "Nanoparticles" are herein defined as particles with an average particle diameter of between 1 and 100 nm. Preferably, the average particle diameter of the particles is between about 1 and 40 nm. As used herein, "particle size" and "particle diameter" have the same meaning. The nanoparticles include, but are not limited to metallic, semiconductor, or polymer particles. The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc sulfide, zinc selenide, lead sulfide, gallium arsenide, silicon, tin oxide, iron oxide, and indium phosphide. "The polymer nanoparticles" include, but not limited to polystyrene, polymethacrylate, polyethylene glycol and polysiloxane.

As used herein a "nucleic acid molecule" is defined as a polymer of RNA, DNA, or peptide nucleic acid (PNA) that is single- or double-stranded, optionally containing synthetic, non-natural or altered nucleotide bases. A nucleic acid molecule in the form of a polymer of DNA may be comprised of one or more segments of cDNA, genomic DNA or synthetic DNA.

The letters "A", "G", "T", "C" when referred to in the context of nucleic acids will mean the purine bases adenine ($C_5H_5N_5$) and guanine ($C_5H_5N_5O$) and the pyrimidine bases thymine ($C_5H_6N_2O_2$) and cytosine ($C_4H_5N_3O$), respectively.

All ranges given herein include the end of the ranges and also all the intermediate range points.

The instant invention provides hair coloring and cosmetic compositions comprising chemically modified and physically modified carbon nanotubes.

Carbon Nanotubes

The term "carbon nanotube" refers to a hollow article composed primarily of carbon atoms. Carbon nanotubes of the invention are generally about 0.5 to 2 nm in diameter where the ratio of the length dimension to the narrow dimension (diameter), i.e., the aspect ratio, is at least 5. In general, the aspect ratio is between 10 and 2000. Carbon nanotubes are comprised primarily of carbon atoms, however they may be doped with other elements, e.g., metals. The carbon-based nanotubes of the invention can be either multi-walled nanotubes (MWNTs) or single-walled nanotubes (SWNTs). A MWNT, for example, includes several concentric nanotubes each having a different diameter. Thus, the smallest diameter tube is encapsulated by a larger diameter tube, which in turn, is encapsulated by another larger diameter nanotube. A SWNT, on the other hand, includes only one nanotube.

Carbon nanotubes may be produced by a variety of methods, and are commercially available, for example from Carbon Nanotechnologies Inc. (Houston, Tex.) and Carbon Solutions Inc. (Riverside, Calif.). Methods of CNT synthesis include laser vaporization of graphite (A. Thess et al. *Science* 273, 483 (1996)), arc discharge (C. Journet et al., *Nature* 388, 756 (1997)) and HiPCo (high pressure carbon monoxide) process (P. Nikolaev et al. *Chem. Phys. Lett.* 313, 91-97 (1999)). Chemical vapor deposition (CVD) can also be used in producing carbon nanotubes (J. Kong et al. *Chem. Phys. Lett.* 292, 567-574 (1998); J. Kong et al. *Nature* 395, 878-879 (1998); A. Cassell et al. *J. Phys. Chem.* 103, 6484-6492 (1999); and H. Dai et al. *J. Phys. Chem.* 103, 11246-11255 (1999)).

Additionally CNTs may be grown via catalytic processes both in solution and on solid substrates (Yan Li, et al., *Chem. Mater.* 13(3), 1008-1014 (2001); N. Franklin and H. Dai *Adv. Mater.* 12, 890 (2000); and A. Cassell et al. *J. Am. Chem. Soc.* 121, 7975-7976 (1999)). Most CNTs, as presently prepared, are in the form of entangled tubes. Individual tubes in the product differ in diameter, chirality, and number of walls. Moreover, long tubes show a strong tendency to aggregate into "ropes" held together by Van der Waals forces. These ropes are formed due to the large surface areas of nanotubes and can contain tens to hundreds of nanotubes in one rope.

Physically Modified Carbon Nanotubes

Carbon nanotubes may be physically modified by any means known in the art, including, but not limited to ultrasonication or coating with a modifying agent. Suitable, modifying agents include, but are not limited to surfactants, such as sodium dodecylsulfate, alkyl benzene sulfonate, dextrin, polyethylene oxide, alkyl-ether sulfonate and Triton® series compounds; and organic polymers, such as polyamines, anionic polymers, cationic polymers, polyvinylpyrrolidone, polysaccharides, gum arabic, and polystyrene sulfonate; biopolymers, such as peptides, proteins and nucleic acids; and nanoparticles. Physical modification of the nanotubes accomplishes two purposes. First, the modifying agent forms a place of attachment for ligands or for a hair substrate. Secondly, the modifying agent often disperses the nanotubes allowing for facile handling. Many of these modification techniques are reviewed by Hilding, J., et al. (*Journal of Dispersion Science and Technology* (2003), 24(1), 1-41).

In one embodiment, carbon nanotubes may be physically modified by coating with biopolymers, such as peptides, proteins, and nucleic acids. A method for physically modifying carbon nanotubes using nucleic acids is described in U.S. Patent Application Publication Nos. 2004/0132072 and 2005/0009039, incorporated herein by reference. The nucleic acid molecules may be of any type and from any suitable source and include but are not limited to DNA, RNA and peptide nucleic acids. The nucleic acid molecules may be either single stranded or double stranded and may optionally be functionalized at any point with a variety of reactive groups, ligands or agents. The nucleic acid molecules of the invention may be generated by synthetic means or may be isolated from nature by protocols well known in the art (Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989)).

Where nucleic acids are used as a modifying agent it should be noted that no additional chemical functionalization of the carbon nanotube is necessary. Biopolymers generally have a native affinity for carbon nanotubes and the presence of additional functional groups on the surface of the carbon nanotube is not needed to effect good binding and dispersion.

Alternatively, the carbon nanotubes of the invention may be modified using synthetic organic polymers. Methods for associating such polymers with carbon nanotubes are discussed in M. O'Connell et al., *Chem. Phys. Lett.*, 342, 265, 2001; and WO 02/076888 herein incorporated by reference.

In another embodiment, the CNT's of the invention may be physically modified with nanoparticles. Where nanoparticles are used, it is preferred if they are first surfaced functionalized to bind to the CNT. For example, the nanoparticles may be stabilized and made water-soluble by the use of a suitable organic coating or monolayer. The surface modification of nanoparticles can also produce stabilized, charged, water-soluble semiconductor nanoparticles.

Methods of functionalizing nanoparticles are provided in the art. One method involves the use of a suitable organic coating or monolayer. These particles can be either charged or neutral depending on the nature of the organic coating. For example, Templeton et al. (*Langmuir* 15:66-76 (1999)), herein incorporated by reference, describe a method for the preparation of stabilized, charged, water-soluble gold nanoparticles protected by tiopronin or coenzyme A monolayers. To prepare the tiopronin-protected gold nanoparticles, tetrachloroauric acid and N-(2-mercaptopropionyl)glycine (tiopronin) were codissolved in a mixture of methanol and acetic acid. Sodium borohydride was added with rapid stirring. The average particle size of these particles could be controlled by varying the mole ratio of tiopronin to tetrachloroauric acid in the reaction. The coenzyme A protected gold nanoparticles were prepared in a similar manner by substituting coenzyme A for tiopronin in the reaction.

A similar method of preparing stabilized, water-soluble nanoparticles of the metals gold, silver, platinum, palladium, cobalt and nickel is descried by Heath et al. in U.S. Pat. No. 6,103,868, herein incorporated by reference. In this method, a solution or dispersion of one or more metal salts was mixed with a solution of an organic surface passivant that had a functional group such as a thiol, phosphine, disulfide, amine, oxide, or amide. A reducing agent was then added to reduce the metal salt to the free metal.

In a preferred method, nanoparticles may be coated with a monolayer as described in U.S. Patent Application Publication No. 2004/0058457, incorporated herein by reference. In this method nanoparticles coated with a monolayer that is functionalized to receive a bi-functional protein. The bifunctional protein binds at one domain to the surface of the nanoparticle and at a second domain to another moiety such as a nucleic acid, a protein or a CNT.

The functionalized nanoparticles can interact with carbon nanotubes to modify the carbon nanotubes through the methods of hydrophobic interaction and electrostatic binding and provide potential attachment sites for hair.

Chemically Functionalized Carbon Nanotubes

Carbon nanotubes may be chemically functionalized using methods known in the art. The chemical functionalization of the carbon nanotube surface results in functional groups, including but not limited to —COOH, —PO$_4^-$, —SO$_3^-$, —SO$_3$H, —SH, NH$_2$, tertiary amines, quaternized amines, —CHO, or —OH.

The undispersed carbon nanotubes may be oxidized according to the methods described by Niu et al. in U.S. Patent Application Publication Nos. 2003/0039604 and 2003/0086858, both of which are incorporated herein by reference. For example, the undispersed carbon nanotubes may be oxidized by contacting them with a radical generating agent, including but not limited to ammonium persulfate ((NH$_4$)$_2$S$_2$O$_8$), sodium persulfate (Na$_2$S$_2$O$_8$), or potassium persulfate (K$_2$S$_2$O$_8$) in an acid. Suitable acids include, but are not limited to sulfuric acid, nitric acid, hydrochloric acid, or trifluoroacetic acid. This oxidation results in the generation of surface —COOH, —CHO, and —OH groups on the carbon nanotubes.

Chemical Functionalization Via Radical Initiation Reactions

CNT's may additionally be functionalized using free radical organic initiator, such as azo-initiators. A specific reaction mechanism is shown in FIG. 1 and is illustrative of the general principal. Carbon nanotubes are hollow tubes with a conjugated surface structure (C=C bonds). 2,2'-Azobis(4-cyanovaleric acid) is decomposed at temperatures of about 70° C. to form free radicals. The free radicals attack the double bond (C=C) on carbon nanotubes to form single C—C bonds. This functionalization of the carbon nanotube surface allows for the covalent linking of the CNT with other molecules. Such functionalized carbon nanotubes may be dispersed in organic and aqueous solutions. The free radical functionalization of the carbon nanotube surface results in functional groups, including but not limited to —COOH, —PO$_4^-$, —SO$_3^-$, —SO$_3$H, —SH, NH$_2$, tertiary amines, quaternized amines, —CHO, or —OH.

Chemical Functionalization Via Diels-Alder Reactions

The Diels-Alder reaction is a chemical reaction between a conjugated molecule and a C=C bond molecule under certain conditions, as shown below.

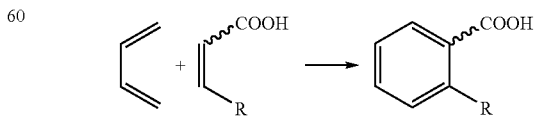

Since carbon nanotubes have a conjugated surface structure, this reaction can be adopted to chemically attach functional groups on the carbon nanotube surface to disperse the CNT's in organic or aqueous solutions. Chemical functionalization by Diels-Alder reaction results in functional groups on carbon nanotubes, including but not limited to —COOH, —$PO_4^-$, —$SO_3^-$, —$SO_3H$, —SH, $NH_2$, tertiary amines, quaternized amines, —CHO, or —OH.

Hair Colorant Compositions

The hair colorant compositions of the invention comprise an effective amount of physically modified or chemically functionalized carbon nanotubes in a cosmetically acceptable medium. An effective amount of physically modified or chemically functionalized carbon nanotubes for use in hair colorant compositions is herein defined as a proportion of from about 0.001% to about 20% by weight relative to the total weight of the composition. Components of a cosmetically acceptable medium for hair colorant compositions are well known in the art (see for example Dias et al., in U.S. Pat. No. 6,398,821, Deutz et al., in U.S. Pat. No. 6,129,770, and Bogaty et al. in U.S. Pat. No. 4,559,057, all of which are incorporated herein by reference). For example, hair colorant compositions may be aqueous solutions or aqueous alcoholic solutions and may contain sequestrants, stabilizers, thickeners, buffers, carriers, surfactants, solvents, antioxidants, polymers, and conditioners. In contrast to oxidative hair colorant compositions, which require strong alkaline conditions, the hair colorant compositions of the invention may have a neutral pH, i.e., pH 6 to 8.

Methods for Dyeing Hair

The present invention also provides methods for coloring hair by applying a hair colorant composition comprising an effective amount of physically modified or chemically functionalized carbon nanotubes to the hair by various means, including, but not limited to spraying, brushing, and applying by hand. The hair colorant composition is allowed to contact the hair for a period of time sufficient for the carbon nanotubes to bind to the hair, typically between about 5 to about 50 min, and then the excess hair colorant composition may be rinsed from the hair. In addition to coloring hair, the peptide-based carbon nanotube colorants of the invention provide a volumizing (i.e., thickening) effect on the hair.

In one embodiment, the application of the hair colorant composition to the hair is repeated one or more times.

Figure 2:
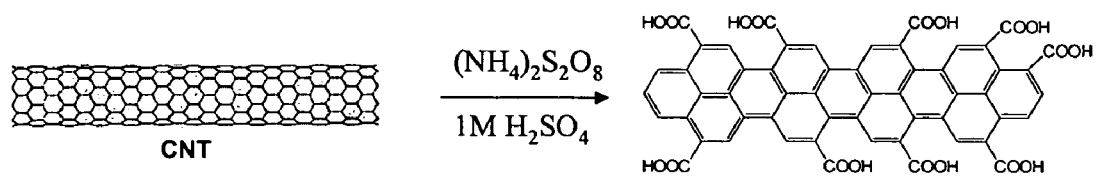
FIG. 2. A cartoon showing a process of hair coloring with carbon nanotubes and polyamines: (1) chemically functionalizing carbon nanotubes and dispersing the carbon nanotubes in water; and (2) applying a polyamine coating to hair surface, then followed by coating carbon nanotubes.
Figure 2:
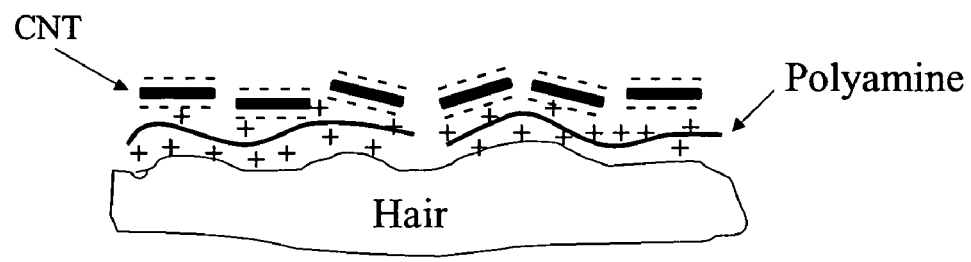

In another embodiment, the hair may be first coated with a polymer and then contacted with a functionalized CNT as depicted in FIG. 2. Referring to FIG. 2, the carbon nanotube is first functionalized via an oxidation process to produce an excess of COOH groups on the surface. The hair is then treated with a polymer that has affinity for the functionalized CNT. Polymers suitable for this purpose, include but are not limited to polyamines, anionic polymers, and cationic polymers. The polymer treated hair is then contacted with the functionalized CNT for a time sufficient to permit binding of the CNT and dying of the hair.

Figure 3:
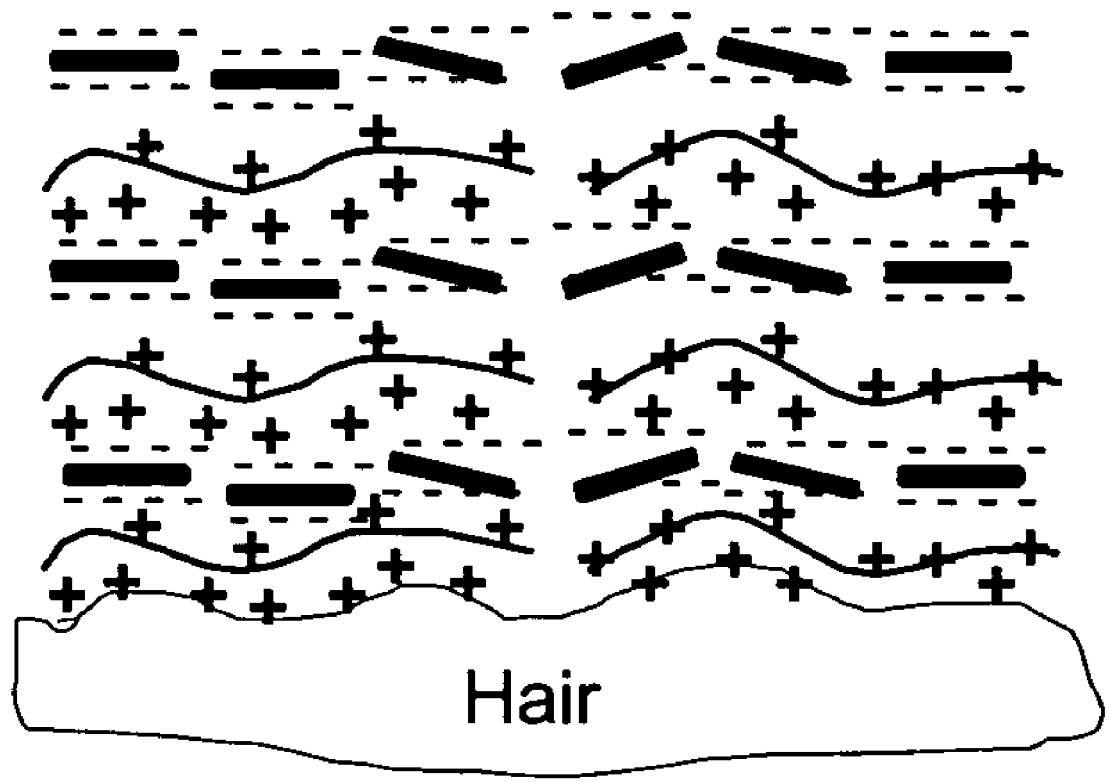
FIG. 3. A cartoon showing a process of hair coloring by constructing multiple layers of carbon nanotubes alternated with multiple layers of polyamines.

The process of pre-treating hair with a polymer to enhance CNT binding may also be used to control the darkness or shade of the color of the hair through a layering effect as shown in FIG. 3. Referring to FIG. 3, the hair, is alternately treated with polymer followed by the CNT hair coloring compositions any number of times and at each cycle of polymer-CNT application a new layer of CNT's will be formed.

Cosmetic Compositions

The physically modified or chemically functionalized carbon nanotubes of the invention may also be used as coloring agents in cosmetic compositions including, but not limited to eye shadow, eyeliner, eyebrow pencil, and mascara.

Cosmetic compositions containing pigments are well known in the art (see for example, Philippe in U.S. Pat. No. 6,280,747, Arraudeau et al. in U.S. Pat. No. 5,053,220, and Grimm et al. in U.S. Patent Application Publication No. 2002/0034480, all of which are incorporated herein by reference).

In one embodiment, the cosmetic composition is an anhydrous make-up product comprising a cosmetically acceptable medium which contains a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. In another embodiment, the cosmetic composition may be in the form of a stable dispersion such as a water-in-oil or oil-in-water emulsion. In both types of compositions, the proportion of physically modified or chemically functionalized carbon nanotubes is generally from about 0.001% to about 20% by weight relative to the total weight of the composition.

Methods for Coloring Eyebrows or Eyelashes

The present invention also provides a method for coloring eyebrows or eyelashes by contacting a cosmetic composition comprising an effective amount of physically modified or chemically functionalized carbon nanotubes to the eyebrows or eyelashes by various means, including, but not limited to spraying, brushing, and applying by hand. The cosmetic composition is allowed to contact the eyebrows or eyelashes for a period of time sufficient for the carbon nanotubes to bind to the eyebrows or eyelashes. Typically, the composition is left on after the application. In addition to coloring eyebrows and eyelashes, the peptide-based carbon nanotube colorants of the invention provide a volumizing (i.e., thickening) effect on the eyebrows and eyelashes.

In one embodiment, the application of the cosmetic composition to the eyebrows or eyelashes is repeated one or more times.

In another embodiment, the eyebrows or eyelashes are first coated with a polymer, including but not limited to polyamines, anionic polymers, and cationic polymers, prior to contact with the cosmetic composition. In another embodiment, the process of coating the eyebrows or eyelashes with a polymer, followed by contacting with the cosmetic composition is repeated one or more times.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "mL" means milliliter(s), "L" means liter(s), "μL" means microliter(s), "μm" means micrometer(s), "mol" means mole(s), "mmol" means millimole(s), "g" means gram(s), "mg" means milligram(s), "ppm" means parts per million, "M" means molar concentration. "rpm" means revolutions per minute, "Mw" means weight-average molecular weight, "qs" means as much as suffices.

Example 1

Preparation of Chemically Functionalized Carbon Nanotubes

The purpose of this Example was to prepare chemically functionalized carbon nanotubes. The carbon nanotubes were treated with ammonium persulfate in sulfuric acid.

Multi-walled carbon nanotubes (50 mg, HiPCo from Carbon Nanotechnologies Inc., Houston, Tex.) were added to a 50 mL beaker and mixed with 5.0 g of ammonium persulfate (98% from Aldrich, Milwaukee, Wis.) and 15.0 mL of a 1.0 M $H_2SO_4$ (98%, GR grade from EM Science, Gibbstown, N.J.) aqueous solution by stirring with a magnetic stir plate at room temperature for 48 h. The reaction mixture was transferred into two 15 mL plastic centrifuge tubes and centrifuged at 8,500 rpm for 2 min. The supernatant became clear and was removed. The product was washed with water 5 times using centrifugation to collect the nanotubes. The time required to centrifuge the nanotubes increased with each wash, indicating that the size of the nanotubes was in the nanometer range. The final centrifugation required 60 min. The chemically functionalized carbon nanotubes dispersed in water so well that they were not spun down by centrifuging at 12,500 rpm for 20 min. The final product was near neutral (pH=6.0) and was dried by lyophilization for 24 h. The dried carbon nanotubes were readily dispersed in water.

Example 2

Coloring Normal White Hair with Chemically Functionalized Carbon Nanotubes

The purpose of this Example was to dye a sample of natural white hair using the chemically functionalized carbon nanotubes prepared in Example 1.

A bundle of natural white hair (approximately 100 pieces) (from International Hair Importers and Products Inc., Bellerose, N.Y.) was cleaned by mixing with 10 mL of 50% isopropanol for 30 min to remove the oily or greasy material from the hair surface, and then washed at least 5 times with distilled water. After drying in air, the cleaned hair was immersed for 10 min in a solution containing 5 mg of chemically functionalized carbon nanotubes, prepared as described in Example 1, dissolved in 10 mL of distilled water. After dying, the hair was washed at least 5 times with distilled water. The original natural white hair became light black. The dyed hair was washed three times with a 30% shampoo solution (Pantene Pro-V shampoo, Proctor & Gamble, Cincinnati, Ohio) by immersing the hair in the shampoo solution and stirring with a glass pipette. The hair was then rinsed at least 10 times with distilled water. The final color of the dyed, natural white hair was very light black.

Example 3

Coloring Beached Hair with Chemically Functionalized Carbon Nanotubes

The purpose of this Example was to dye a sample of bleached, natural white hair using the chemically functionalized carbon nanotubes prepared in Example 1.

To prepare a bleached hair sample, natural white human hair (International Hair Importers and Products Inc.) was placed in 6% $H_2O_2$, which was adjusted to pH 10.2 with ammonium hydroxide, for 10 min at room temperature. The hair sample was then washed 5 times for 5 min each with deionized water, and air-dried overnight at room temperature. A bundle of bleached natural white hair (approximately 100 pieces) was immersed for 10 min in a solution containing 5 mg of chemically functionalized carbon nanotubes, prepared as described in Example 1, dissolved in 10 mL of distilled water. The hair sample was air-dried and then washed at least 5 times with distilled water. The original bleached, white hair became black. The dyed hair was washed three times with a 30% shampoo solution (Pantene Pro-V shampoo) by immersing the hair in the shampoo solution and stirring with a glass pipette. The hair was then rinsed at least 10 times with distilled water. The final color of the dyed, natural white hair was light black.

Example 4

Coloring Hair with Chemically Functionalized Carbon Nanotubes Enhanced by Polyamines The purpose of this Example was to dye a sample of bleached, natural white hair with the chemically functionalized carbon nanotubes enhanced with a polyamine coating.

A bleached hair sample was prepared as described in Example 3. A bundle of the bleached, natural white hair (approximately 100 pieces) was immersed for 10 min in 5% poly(allylamine) aqueous solution (prepared from 20 wt % poly(allylamine) in water, average Mw approximately 65,000 from Aldrich), and then washed 5 times (1 min for each wash) by flushing with copious amounts of distilled water. The poly(allylamine)-coated hair was air-dried, and then immersed in a solution containing 5 mg of chemically functionalized carbon nanotubes, prepared as described in Example 1, dissolved in 10 mL of distilled water. After dyeing, the hair was washed at least 5 times with distilled water. The hair color was changed to light black. The dyed hair was washed 3 times with a 30% shampoo solution (Pantene Pro-V shampoo) by immersing the hair in the shampoo solution and stirring with a glass pipette for 5 min each time. The hair was then rinsed at least 5 times with distilled water. This shampoo washing process did not change the hair color, i.e. the hair remained light black.

Example 5

Coloring Hair with Multiple Layers of Chemically Functionalized Carbon Nanotubes and Polyamines The purpose of this Example was to dye a sample of bleached, natural white hair with multiple layers of the chemically functionalized carbon nanotubes alternating with polyamine layers.

A bleached hair sample was prepared as described in Example 3. A bundle of the bleached, natural white hair (approximately 100 pieces) was immersed for 10 min in 5% poly(allylamine) aqueous solution (prepared from 20 wt % poly(allyamine) in water, average Mw approximately 65,000 from Aldrich), and then washed 5 times (1 min for each wash) by flushing with copious amounts of distilled water. The poly(allylamine)-coated hair was air-dried, and then immersed in a solution containing 5 mg of chemically functionalized carbon nanotubes, prepared as described in Example 1, dissolved in 10 mL of distilled water. After dyeing, the hair was washed at least 5 times with distilled water. This dyeing cycle (coating with polyamine and washing, then dyeing with carbon nanotubes and washing) was repeated 4 more times. The hair color changed from white to dark black with increasing number of dyeing cycles. After the first cycle of dyeing, the hair color changed from white to light black. After 4 cycles of dyeing, the hair was dark black. Further dyeing cycles did not change the hair color. The dyed hair with layers of carbon nanotubes and polyamines was washed 3 times with a 30% shampoo solution (Pantene Pro-V shampoo) by immersing the hair in the shampoo solution and stirring with a glass pipette for 5 min each time. The hair was then rinsed at least 5 times with distilled water. This shampoo washing process did not change the hair color, i.e. the hair remained dark black.

Example 6

Mascara Composition in Emulsion Form Containing Chemically Functionalized Carbon Nanotubes The purpose of this prophetic Example is to describe the preparation of a mascara composition in emulsion form containing chemically functionalized carbon nanotubes.

The mascara composition is prepared using the following ingredients:

| Chemical or Trade Name | Amount, g |
| --- | --- |
| Triethanolamine stearate | 10 |
| Beeswax | 17 |
| Candelilla wax | 15 |
| Xanthane gum | 1 |
| Propyl para-hydroxybenzoate | 0.15 |
| Chemically functionalized carbon nanotubes, prepared as described in Example 1 | 5 |
| Water | qs to 100 |

The waxes are melted. The aqueous phase containing the gums and the chemically functionalized carbon nanotubes is heated to the same temperature as the waxes. The two phases are mixed and stirred vigorously.

Example 7

Mascara Composition in Cake Form Containing Chemically Functionalized Carbon Nanotubes The purpose of this prophetic Example is to describe the preparation of a mascara composition in cake form containing chemically functionalized carbon nanotubes.

The mascara composition is prepared using the following ingredients:

| Chemical or Trade Name | Amount, g |
| --- | --- |
| Stearic acid, triple-pressed | 33 |
| Triethanolamine | 12 |
| Glycerol monostearate, self emulsifying | 6 |
| Beeswax | 17 |
| Carnauba wax | 10 |
| Lanolin | 2.8 |
| Castor oil | 6 |
| Propyl para-hydroxybenzoate | 0.2 |
| Chemically functionalized carbon nanotubes, prepared as described in Example 1 | 13 |

The waxes, propyl para-hydroxybenzoate, lanolin and castor oil are melted together in a heated mixing kettle, the carnauba wax being added first. The chemically functionalized carbon nanotubes are then stirred in and the resulting mass is put through a heated roller mill to ensure adequate dispersion. The mixture is returned to the kettle and the Glycerol monostearate, and the triethanolamine are added sequentially. When mixing is complete, the kettle is allowed to cool. Then, the mixture is reheated with slow mixing to avoid the incorporation of air bubbles, and then poured into prepared molds.

Example 8

Eyebrow Pencil Composition Containing Chemically Functionalized Carbon Nanotubes The purpose of this prophetic Example is to describe the preparation of an eyebrow pencil composition containing chemically functionalized carbon nanotubes.

The eyebrow pencil composition is prepared using the following ingredients:

| Chemical or Trade Name | Amount, g |
| --- | --- |
| Carnauba wax | 8 |
| Ozokerite | 14 |
| Beeswax | 10 |
| Microcrystalline wax | 14 |
| Hydrogenated oil | 7 |
| Mineral oil | 18 |
| Petrolatum | 18 |
| Lanolin, anhydrous | 2 |
| Propyl para-hydroxybenzoate | 0.3 |
| Chemically functionalized carbon nanotubes, prepared as described in Example 1 | 8.5 |
| Ultramarine | 0.2 |

The chemically functionalized carbon nanotubes are incorporated into the base wax and dispersed by triple-roll milling, as described in Example 7. The remaining ingredients are added sequentially. When mixing is complete, the mixture is allowed to cool and then is carefully reheated and stirred, and poured into suitable molds.

Example 9

Hair Colorant Composition Containing Chemically Functionalized Carbon Nanotubes

The purpose of this prophetic Example is to describe the preparation of a hair colorant composition containing chemically functionalized carbon nanotubes.

The hair colorant composition is prepared using the following ingredients:

| Chemical or Trade Name | wt % |
| --- | --- |
| Ammonium lauryl sulfate (anionic surfactant) | 2.00 |
| Propylene glycol (moisturizer) | 4.00 |
| Ethoxydiglycol (solvent) | 2.00 |
| Seaweed extract (conditioner) | 0.80 |
| Tetrasodium EDTA (chelating agent) | 0.80 |
| Isoascorbic acid (antioxidant) | 0.20 |
| Oleic acid (soap) | 12.50 |
| Cetearyl alcohol (opacifier) | 4.00 |
| Emulsifying wax (emulsifier) | 2.00 |
| Oleth-20 (nonionic surfactant) | 1.00 |
| Steareth-21 (nonionic surfactant) | 0.70 |

-continued

| Chemical or Trade Name | wt % |
|---|---|
| Meadowfoam seed oil (oil) | 0.75 |
| Oleyl alcohol (oil) | 0.40 |
| Polyquaternium-10 (cationic surfactant) | 0.20 |
| Polyquaternium-28 (cationic surfactant) | 0.50 |
| Chemically functionalized carbon nanotubes, prepared as described in Example 1 | 0.30 |
| Cibafast ® W liquid[2] (UV absorber) | 1.00 |
| Fragrance | 0.75 |
| Wheat amino acids solution | 1.00 |
| Water | qs to 100 |

What is claimed is:

1. A method for coloring hair, eyebrows or eyelashes comprising the sequential steps of:

a) applying a polymer composition to hair, eyebrows or eyelashes to form a first polymer treated layer;

b) contacting the first polymer treated layer of step (a) with a chemically functionalized carbon nanotube to form a first colorant layer;

c) applying a polymer composition to the first colorant layer of step (b) to form a second polymer treated layer;

d) contacting the second polymer treated layer of step c) with a chemically functionalized carbon nanotube to form a second colorant layer; and e) optionally, repeating steps (a)-(d) one or more times.

2. A method according to claim 1 wherein the polymer is selected from the group consisting of polyamines, anionic polymers, and cationic polymers.

* * * * *